(12) United States Patent
Beister et al.

(10) Patent No.: US 11,935,161 B2
(45) Date of Patent: Mar. 19, 2024

(54) METHOD FOR GENERATING RESULT SLICE IMAGES WITH AT LEAST PARTIALLY DIFFERENT SLICE THICKNESS

(71) Applicant: Siemens Healthcare GmbH, Erlangen (DE)

(72) Inventors: Marcel Beister, Erlangen (DE); Ludwig Ritschl, Buttenheim (DE); Steffen Kappler, Effeltrich (DE); Mathias Hoernig, Moehrendorf (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 314 days.

(21) Appl. No.: 17/487,531

(22) Filed: Sep. 28, 2021

(65) Prior Publication Data
US 2022/0101573 A1 Mar. 31, 2022

(30) Foreign Application Priority Data

Sep. 30, 2020 (DE) ...................... 10 2020 212 403.5
Sep. 16, 2021 (DE) ...................... 10 2021 210 289.1

(51) Int. Cl.
*G06T 7/00* (2017.01)
*A61B 6/00* (2006.01)
(Continued)

(52) U.S. Cl.
CPC ............ *G06T 11/008* (2013.01); *A61B 6/025* (2013.01); *A61B 6/502* (2013.01); *A61B 6/5223* (2013.01);
(Continued)

(58) Field of Classification Search
CPC ........... G06K 9/00261; G06K 9/00288; G06K 9/00228; G06K 9/00268; G06K 9/00281; G06K 9/6202; G06K 2009/4666; G06K 9/00362; G06K 9/4642; G06K 9/6206; G06K 9/6255; G06K 9/6256; G06K 9/00275; G06K 9/00308; G06K 9/00926; G06K 9/3233; G06K 9/4671;
(Continued)

(56) References Cited

U.S. PATENT DOCUMENTS

| 9,460,508 B2 * | 10/2016 | Gkanatsios ............ A61B 6/025 |
| 10,248,882 B2 * | 4/2019 | Ren .......................... G06T 7/30 |
| 2014/0294138 A1 * | 10/2014 | Jerebko ................... A61B 6/025 378/4 |

* cited by examiner

*Primary Examiner* — Quan M Hua
(74) *Attorney, Agent, or Firm* — Harness, Dickey & Pierce, P.L.C.

(57) ABSTRACT

A method for generating result slice images with at least partially different slice thickness based on a tomosynthesis image data set of a breast includes generating average value slices and maximum value slices (MIP) based on the tomosynthesis image data set, frequency dividing the average value slices into low-pass filtered and high-pass filtered average value slices, high-pass filtering of maximum value slices to form high-pass filtered maximum value slices, mixing high-pass filtered maximum value slices and high-pass filtered average value slices to form mixed high-pass filtered maximum value slices, combining the low-pass filtered average value slices with the mixed high-pass filtered maximum value slices to form the result slice images, and applying a moving maximum value across a selected thickness of maximum value slices or across a selected thickness of mixed high-pass filtered maximum value slices.

20 Claims, 3 Drawing Sheets

(51) Int. Cl.
*A61B 6/02* (2006.01)
*G06T 5/20* (2006.01)
*G06T 11/00* (2006.01)

(52) U.S. Cl.
CPC .............. *A61B 6/5235* (2013.01); *G06T 5/20* (2013.01); *G06T 2207/10112* (2013.01); *G06T 2207/30068* (2013.01)

(58) Field of Classification Search
CPC .. G06K 9/6215; G06K 9/6228; G06K 9/6262; G06K 9/627; G06K 9/6276; G06K 9/629; G06N 3/0454; G06N 3/084; G06N 3/08; G06T 11/00; G06T 2207/10016; G06T 2207/10024; G06T 2207/20081; G06T 2207/30201; G06T 2207/30241; G06T 2207/30244; G06T 7/251; G06T 7/74; G06T 7/80

See application file for complete search history.

30  31

40  41

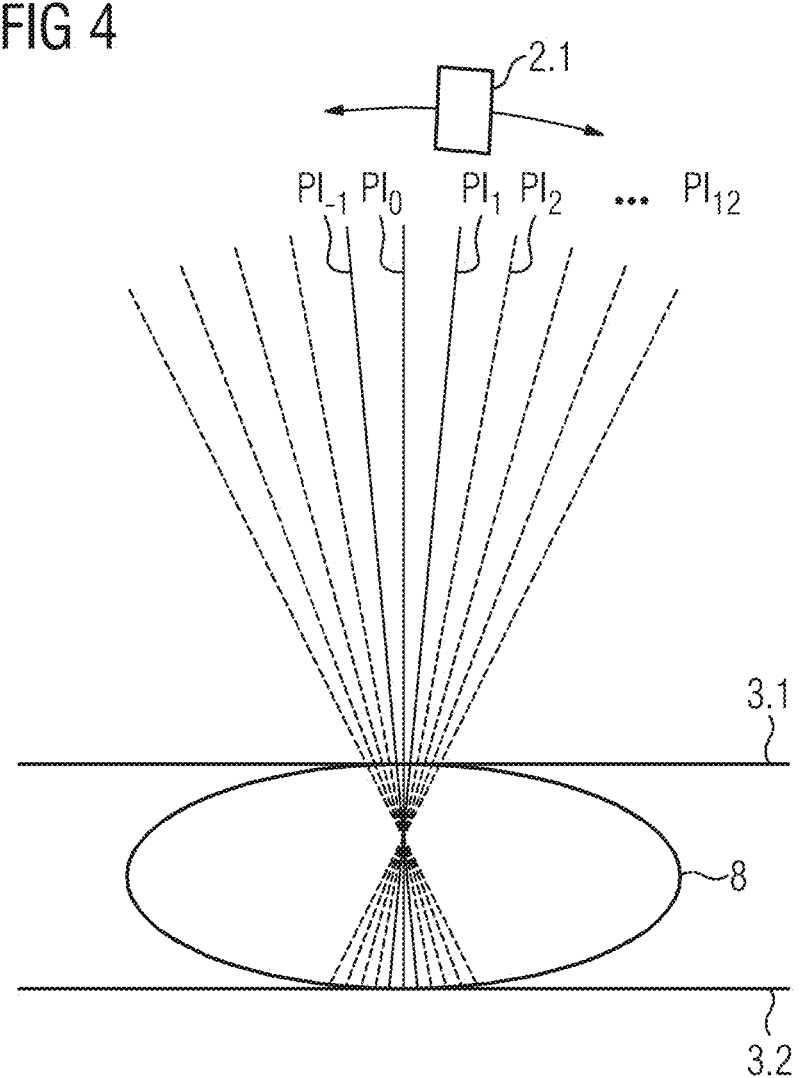

METHOD FOR GENERATING RESULT SLICE IMAGES WITH AT LEAST PARTIALLY DIFFERENT SLICE THICKNESS

PRIORITY STATEMENT

The present application hereby claims priority under 35 U.S.C. § 119 to German patent application numbers DE 102020212403.5 filed Sep. 30, 2020 and DE 102021210289.1 filed Sep. 16, 2021, the entire contents of each of which are hereby incorporated herein by reference.

FIELD

At least one example embodiments relates to a method for generating result slice images with at least partially different slice thickness.

RELATED ART

Digital breast tomosynthesis (DBT) allows three-dimensional imaging of the breast. A plurality of slices in different positions, in particular heights, of the breast are reconstructed from a large number of projection data sets, for example 25. A projection data set is recorded at a projection angle. The projection data sets are recorded for different projection angles. The different projection angles can in particular be recorded in a limited angular range of, for example, 50 degrees.

The depiction of microcalcifications in the reconstructed slice images of a small-angle X-ray tomosynthesis recording (for example 15-degree angle) is frequently perceived as better or clearer than depiction in a wide-angle recording (for example 50-degree angle), although the depth resolution in the slice images is higher due to the greater angular coverage.

SUMMARY

However, this can limit the visibility of small microcalcifications to only very few slice images, resulting in only a very brief "flare-up" of the microcalcification when switching rapidly between the slice images. Furthermore, microcalcifications are obtained via the reconstruction of high-resolution slices with subsequent recombining by a simple thresholding method. The thresholding method is susceptible to differences in intensity and therefore does not always lead to an optimal result.

At least one example embodiment provides a method, a mammography system, a computer program product and a computer-readable medium that enable improved depiction of microcalcifications.

At least one example embodiment provides a method for generating result slice images with at least partially different slice thickness based on a tomosynthesis image data set of a breast, having the steps of generating, frequency dividing, mixing, combining and applying. The at least partially different slice thickness relates above all to a slice thickness that is embodied differently depending on the frequency. Depending upon the (spatial) frequency, the slice thickness can be selected as greater or smaller and be mixed or combined with other spatial frequencies having a slice thickness different therefrom. In particular, the slice thickness for microcalcifications can be greater than for morphological structures. This can in particular mean that slices in a first slice thickness, for example the morphological structures, can be viewed, wherein microcalcifications in a plurality of adjacent slices can be depicted. Combination can advantageously achieve improved visibility of calcifications. For example, the slice thickness can be at least partially different for each result slice image or one result slice image. The (effective) slice thickness can differ pixel by pixel. For example, for pixels with a large amount of attenuation due to a microcalcification, the moving maximum value with the increased slice thickness can make a stronger contribution, while for other pixels the morphological structures with the (standard) slice thickness can make a stronger contribution.

In the generating step, average value slices (AIP) and maximum value slices (MIP) can be generated based on the tomosynthesis image data set. Average value slices can be generated based on a calculation of a median or another averaging operation. Maximum value slices can be generated by a maximum intensity projection (MIP) in that the voxel with the highest attenuation value, in particular in the volume taken into account, is projected onto a 2D image. Alternatively, maximum value slices can be generated by calculating a percentile or an amplitude-weighted sum.

To calculate maximum value slices with the moving maximum value, the actual slice and a certain number of adjacent slices can be taken into account in each case. For example, slices 8 to 12 can be taken into account for the 10th slice. The number of adjacent slices taken into account can, for example, in each case be 2 in both directions, i.e., +/−2. Therefore, the maximum value within these adjacent slices, here, for example, slices 8 to 12, can be determined for each voxel or pixel and used as a moving maximum value in the maximum intensity projection. If a percentile or an amplitude-weighted sum is used, these types of calculation can be applied to the adjacent slices and the moving maximum value determined in this way.

Sampling can take place in slice thicknesses of 1 mm. A smaller slice thickness can be 2 mm. A greater or increased slice thickness can be 6 mm to 8 mm. Herein, the greater slice thickness can above all relate to the information on micro-calcium deposits, i.e., the effective slice thickness of micro-calcium deposits can correspond to the greater slice thickness, while the result slice images can be depicted with the smaller slice thickness. Hence, the information on the micro-calcium deposits can be visible for 6 to 8 mm while viewing successive result slice images. The greater slice thickness of the micro-calcium deposits can slide across the smaller slice thickness by the moving maximum value.

Based on the tomosynthesis data set, a number N of average value slices and maximum value slices can be generated. Before the moving maximum value is applied, the (effective) slice thickness of the average value slices and the maximum value slices can be the same. After the application of the moving maximum value, the effective slice thickness, i.e., the slice thickness taken into account with regard to attenuation information, the maximum value slices or the mixed high-pass filtered maximum value slices, is increased. The number of average value slices and maximum value slices or mixed high-pass filtered maximum value slices can preferably still be N. After the application of the moving maximum value, the maximum value slices or mixed high-pass filtered maximum value slices can take account of the attenuation information of k adjacent slices, in particular maximum value slices or mixed high-pass filtered maximum value slices. k can be in the range from 1 to 10. Preferably, k can be selected such that the increased slice thickness is approximately 6 to 8 mm.

In the frequency dividing or frequency filtering step, the average value slices (AIP) can be divided into low-pass filtered and high-pass filtered average value slices. The low-pass filtered average value slices can in particular comprise morphological structures.

In the high-pass filtering step, the maximum value slices can be filtered to form high-pass filtered maximum value slices. These can in particular comprise structures with high contrast or their edges and small objects, for example microcalcifications.

In the mixing step, high-pass filtered maximum value slices and high-pass filtered average value slices can be mixed to form mixed high-pass filtered maximum value slices. The mixing ratio can be freely selected or adapted. The mixing ratio can, for example, be 50/50- or 1:1. The mixed high-pass filtered maximum value slices can be displayed alternatively or additionally to the result slice images.

In the combining step, low-pass filtered average value slices can be combined with the mixed high-pass filtered maximum value slices to form the result slice images. Advantageously, the advantages of small slice thicknesses for morphological structures and the advantages of greater slice thicknesses for microcalcifications can be combined. Advantageously, individual microcalcifications per se and a possible grouping of microcalcifications can be identified in a simplified or more clearly depicted manner.

In the applying step, a moving maximum value can be applied across a predetermined thickness of maximum value slices or across a predetermined thickness of mixed high-pass filtered maximum value slices. The moving maximum value can in particular be a maximum value depicting a micro-calcium deposit from a maximum value slice, in particular extracted before application of the moving maximum value, which "runs along" across a plurality of successive result slices. In this way, the micro-calcium deposit and in particular a cluster of micro-calcium deposits can be more easily identified by the viewer. If the micro-calcium deposit were only depicted from the maximum value slice corresponding to the result slice, when viewing many slices in succession, the micro-calcium deposit would be briefly visible in one slice and would be easier to overlook. In addition, the spatial proximity to adjacent micro-calcium deposits in adjacent maximum value slices is easier to identify from the moving maximum value, since micro-calcium deposits from adjacent slices can be at least partially depicted together across one or more of result slices. The predetermined thickness of maximum value slices or the predetermined thickness of mixed high-pass filtered maximum value slices can in particular be a predetermined multiple of the slice thickness of an average value slice. For example, the predetermined thickness of the maximum value slices or the high-pass filtered maximum value slices may be greater by a predetermined factor, in particular compared to the slice thickness of the average value slices. The predetermined thickness or the predetermined multiple or the predetermined factor can be defined in the system or by the user, for example based on a breast thickness or a number of microcalcifications or other conspicuous structures within the region under examination or the breast.

The inventors have identified that the visibility of microcalcifications can be further improved. The concept of high-resolution slices can be applied to improve visibility with wide-angle recording. Here, a plurality of finer slice images can be generated for each output slice and then recombined with logic and combined to form an output slice. Due to the finer slices, it can be achieved that, in at least one of these slices, small microcalcifications are struck "sharply" and the contrast to the surroundings reaches its maximum as a result. The average value (AIP) and the maximum value (MIP) of the high-resolution slices relevant for the output slice are compared with one another and, if the difference is sufficient, the maximum value can be obtained instead of the average value.

The inventors have identified the following aspects. The perceptibility of microcalcifications can be improved by using a different (in particular increased) slice thickness, for very small objects (in particular higher frequencies), while the original slice thickness is retained for large objects (in particular medium to lower frequencies). This can be achieved by using a moving maximum value (moving MIP) across a defined thickness of maximum value slices (MIP slices) before these are combined with the average values in the next step.

A further aspect can be frequency-based combination of the high-resolution slices instead of the previous thresholding method. Here, high-frequency components of both the average value (AIP, short for average intensity projection) and the maximum value (MIP, short for maximum intensity projection) can be mixed together in a specific ratio and then combined with the low and medium-frequency components of the average value.

The solution to the problem can combine the advantages of wide-angle tomosynthesis (in particular better depth resolution) with those of small-angle tomosynthesis (in particular better perceptibility of microcalcifications). This enables lesions to be better differentiated from the surroundings than in pure small-angle tomosynthesis, but without having to forego the good identifiability in the case of microcalcifications.

If the so-called "moving MIP", i.e., the moving maximum value, is only applied to the MIP slices or the maximum value slices, the strength of the effect is reduced since the high-frequency components are then still combined with the high-frequency components of the AIP slices or the average value slices.

Alternatively, the "moving MIP", i.e., the moving maximum value, can also be applied to the combined high-frequency components, i.e., the mixed high-pass filtered maximum value slices in order to intensify the effect. Frequency-based combining can furthermore avoid a limit value for the difference, which increases the stability of the method.

According to at least one example embodiment, mask slices can be generated based on the tomosynthesis image data set. Artifact correction can be performed with respect to large high-contrast objects such as large calcium deposits or calcifications and/or metal. The mask slice can contain large high-contrast objects. According to at least one example embodiment, the mask slices can comprise macrocalcifications or metal objects. According to at least one example embodiment, the mask slices can comprise microcalcifications.

According to at least one example embodiment, the mask slices can be taken into account in conjunction with the maximum value slices. The maximum value slices can in particular show high frequencies, for example micro-calcium deposits and edges of high-contrast objects. Taking the mask images into account enables large high-contrast objects to be suppressed, for example large calcium deposits or metal objects. This can improve the visibility of micro-calcium deposits or microcalcifications.

According to at least one example embodiment, the slice thickness of a result slice image with a small object can be increased. According to at least one example embodiment, the (effective) slice thickness in a result slice image can be increased for a smaller object or a higher spatial frequency or frequency. This means that smaller objects or objects with higher spatial frequencies are transferred to adjacent result slice images. The result slice image can have a (standard) slice thickness. This obtains morphological information from precisely this (standard) slice thickness. With regard to the calcifications or small objects or high frequencies, the information is obtained from a slice thickness larger than the (standard) slice thickness, i.e., also from adjacent slices.

According to at least one example embodiment, the slice thickness of a result slice image with a larger object can correspond to a standard slice thickness. According to at least one example embodiment, the slice thickness in a result slice image for a larger object or a lower to medium spatial frequency can correspond to a standard slice thickness.

Alternatively, for larger objects, the slice thickness can be greater than the standard slice thickness. The, in particular effective, slice thickness for micro-calcium deposits or high frequencies can be greater than or equal to the slice thickness for large objects or medium frequencies, which in turn can be greater than the slice thickness for morphological structures or low frequencies.

The moving maximum value can also be applied to large objects or medium frequencies. The slice thickness for large objects and the slice thickness for microcalcifications can be different. The slice thickness for microcalcifications can in particular be greater than the slice thickness for large objects.

In the applying step, the maximum value, for example of a microcalcification, for example weighted by a Gaussian function, can be taken into account in the result slices. Maximum values further away from the result slice (depth) can be taken into account to a lesser extent than maximum values closer to the result slice (depth).

According to at least one example embodiment, the tomosynthesis data set can comprise projection data sets of a tomosynthesis recording. The tomosynthesis data set can in particular comprise a large number of projection data sets, recorded at a large number of projection angles.

According to at least one example embodiment, the step of generating average value slices (AIP) and maximum value slices (MIP) can comprise back projection of the projection data sets. Based on the projection data sets, a slice image data set can be generated by applying back projection. The average value slices and the maximum value slices can be generated based on the slice image data set.

According to at least one example embodiment, the maximum value, in particular for a microcalcification, can be displayed in a plurality of successive result slice images as a moving maximum value, while the information from the average value slices is in each case only displayed in the associated result slice. In this case, the maximum value can also be combined with an average value.

According to at least one example embodiment, the mixing ratio of the high-pass filtered maximum value slices and high-pass filtered average value slices can be 1:1. Alternatively, the mixing ratio can be freely selected or adapted.

According to at least one example embodiment, in a displaying step, the microcalcifications can be notified optically or acoustically.

Microcalcifications can be indicated or marked in the "main slice" in which they are located, for example, optically, graphically or the like. Herein, the main slice can in particular be the result slice in which the microcalcification is actually located. The result slice (depth) can, therefore, correspond to the depth of the microcalcification. The microcalcification can in particular be marked in the result slice corresponding to the maximum value slice in which the microcalcification is actually present as the maximum value.

The indication or marking can, for example, take place in the image, at the edge of the image, in the DICOM header, a secondary capture or the like, in particular with reference to the coordinates of the "smearing" of an activated moving maximum value of a high-contrast structure or its "moving along" in the adjacent slices. The coordinates can specify both x and y within the slice plane and the slice depth.

The method for determining the moving maximum value itself can be used as an indicator of the detection of a high-contrast structure (for example a micro-calcium deposit). This can take place as follows: with an activated moving maximum value, it can be established whether micro-calcium deposits are present (for example by comparing the slice images with a moving maximum value with those without a moving maximum value). Hence, it is possible to indicate in the slices or image that here such structures are displayed by the moving maximum value. It is now optionally possible to indicate informatively, in particular in advance, the (main) slices in which effects of a moving maximum value occur. The indicator function can be activated or deactivated so users can decide whether they wish to be notified of microcalcifications before viewing the results images or whether they first wish to view the result images impartially and, if necessary, receive the notifications on a repeat viewing. The marking can, for example, be in the form of a color. Alternatively or additionally, the marking can be shown by a graphical object, for example by outlining the microcalcification. When scrolling through the result slices, an acoustic notification of the presence of calcification in the (main) slice can be output to the user in the form of a short tone.

At least one example embodiment further relates to a mammography system for performing a method according to example embodiments. The advantages of the method according to example embodiments can advantageously be transferred to the mammography system.

A plurality of projection data sets can be recorded at a plurality of projection angles. Herein, the X-ray source can in particular be moved along a radius around a point in the breast, wherein a projection data set is recorded at each of the projection angles. During the recording, a patient's breast can be arranged as an examination object between an upper compression element and a lower compression element. The mammography system can further comprise a memory facility, a control facility and a computer unit. The mammography system can further comprise an input unit and an output unit, for example a screen.

At least one example embodiment further provides a computer program product with a computer program, which can be loaded directly into a memory facility of a control facility of an X-ray system, in particular in the form of the mammography system, with program sections for executing all the steps of a method according to example embodiments when the computer program is executed in the control facility of the mammography system.

At least one example embodiment further provides to a computer-readable medium on which program sections that can be read and executed by a computer unit are stored for executing all the steps of a method according to example embodiments when the program sections are executed by the mammography system.

At least one example embodiment further provides a method for generating result slice images with at least partially different slice thickness based on a tomosynthesis image data set of a breast, the method including generating average value slices and maximum value slices based on the tomosynthesis image data set, frequency dividing the average value slices into low-pass filtered and high-pass filtered average value slices, high-pass filtering of first maximum value slices to form high-pass filtered maximum value slices, the first maximum value slices being based on the maximum value slices, mixing the high-pass filtered maximum value slices and the high-pass filtered average value slices to form mixed high-pass filtered maximum value slices, combining the low-pass filtered average value slices with first mixed high-pass filtered maximum value slices to form the result slice images, the first mixed high-pass filtered maximum value slices being based on the mixed high-pass filtered maximum value slices and applying a moving maximum value across a selected thickness of the maximum value slices to generate the first maximum value slices or across a selected thickness of the mixed high-pass filtered maximum value slices to produce the first mixed high-pass filtered maximum value slices.

BRIEF DESCRIPTION OF THE DRAWINGS

The following describes example embodiments in more detail with reference to drawings, in which:

FIG. 4 shows a schematic depiction of a mammography system according to at least one example embodiment.

DETAILED DESCRIPTION OF EXAMPLE EMBODIMENTS

Figure 1:
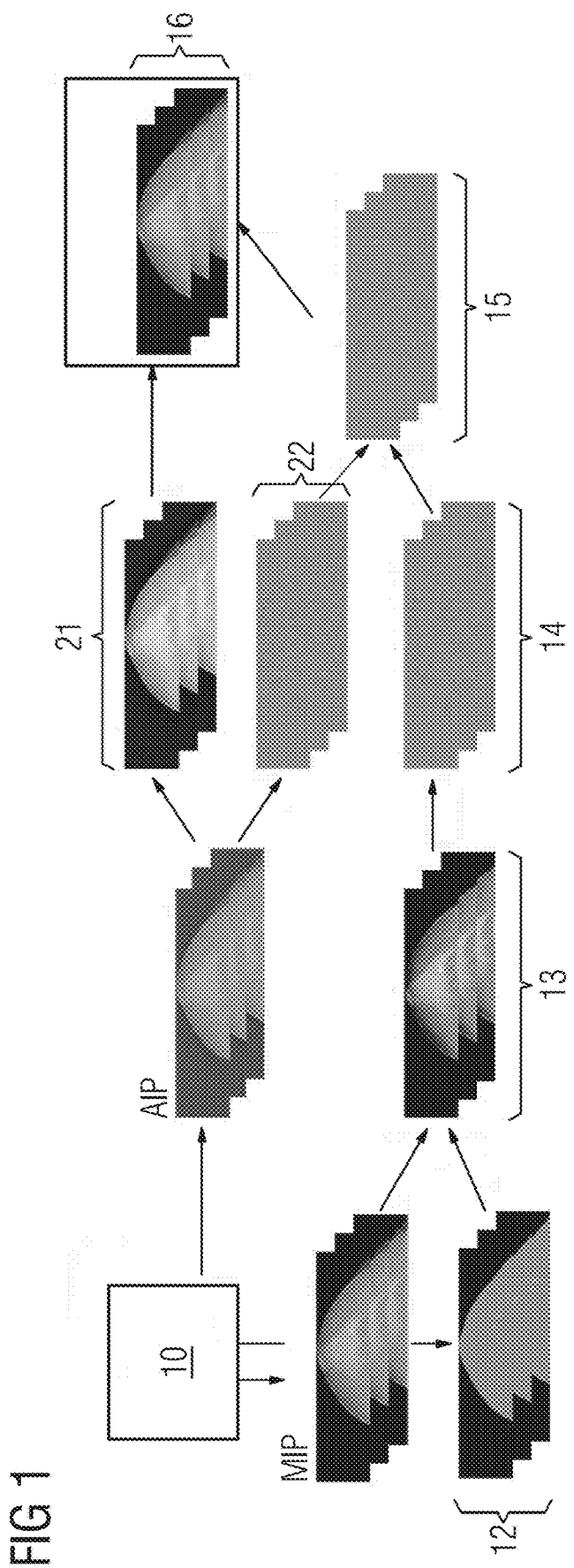
FIG. 1 shows a schematic depiction of a method according to at least one example embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. Example embodiments may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one example embodiment provides a method for generating result slice images with at least partially different slice thickness based on a tomosynthesis image data set of a breast, having the steps of generating, frequency dividing, mixing, combining and applying. The at least partially different slice thickness relates above all to a slice thickness that is embodied differently depending on the frequency. Depending upon the (spatial) frequency, the slice thickness can be selected as greater or smaller and be mixed or combined with other spatial frequencies having a slice thickness different therefrom. In particular, the slice thickness for microcalcifications can be greater than for morphological structures. This can in particular mean that slices in a first slice thickness, for example the morphological structures, can be viewed, wherein microcalcifications in a plurality of adjacent slices can be depicted. Combination can advantageously achieve improved visibility of calcifications. For example, the slice thickness can be at least partially different for each result slice image or one result slice image. The (effective) slice thickness can differ pixel by pixel. For example, for pixels with a large amount of attenuation due to a microcalcification, the moving maximum value with the increased slice thickness can make a stronger contribution, while for other pixels the morphological structures with the (standard) slice thickness can make a stronger contribution.

In the generating step, average value slices (AIP) and maximum value slices (MIP) can be generated based on the tomosynthesis image data set. Average value slices can be generated based on a calculation of a median or another averaging operation. Maximum value slices can be generated by a maximum intensity projection (MIP) in that the voxel with the highest attenuation value, in particular in the volume taken into account, is projected onto a 2D image. Alternatively, maximum value slices can be generated by calculating a percentile or an amplitude-weighted sum.

To calculate maximum value slices with the moving maximum value, the actual slice and a certain number of adjacent slices can be taken into account in each case. For example, slices 8 to 12 can be taken into account for the 10th slice. The number of adjacent slices taken into account can, for example, in each case be 2 in both directions, i.e., +/−2. Therefore, the maximum value within these adjacent slices, here, for example, slices 8 to 12, can be determined for each voxel or pixel and used as a moving maximum value in the maximum intensity projection. If a percentile or an amplitude-weighted sum is used, these types of calculation can be applied to the adjacent slices and the moving maximum value determined in this way.

Sampling can take place in slice thicknesses of 1 mm. A smaller slice thickness can be 2 mm. A greater or increased slice thickness can be 6 mm to 8 mm. Herein, the greater slice thickness can above all relate to the information on micro-calcium deposits, i.e., the effective slice thickness of micro-calcium deposits can correspond to the greater slice thickness, while the result slice images can be depicted with the smaller slice thickness. Hence, the information on the micro-calcium deposits can be visible for 6 to 8 mm while viewing successive result slice images. The greater slice thickness of the micro-calcium deposits can slide across the smaller slice thickness by the moving maximum value.

Based on the tomosynthesis data set, a number N of average value slices and maximum value slices can be generated. Before the moving maximum value is applied, the (effective) slice thickness of the average value slices and the maximum value slices can be the same. After the application of the moving maximum value, the effective slice thickness, i.e., the slice thickness taken into account with regard to attenuation information, the maximum value slices or the mixed high-pass filtered maximum value slices, is increased. The number of average value slices and maximum value slices or mixed high-pass filtered maximum value slices can preferably still be N. After the application of the moving maximum value, the maximum value slices or mixed high-pass filtered maximum value slices can take account of the attenuation information of k adjacent slices, in particular maximum value slices or mixed high-pass filtered maximum value slices. k can be in the range from 1 to 10. Preferably, k can be selected such that the increased slice thickness is approximately 6 to 8 mm.

In the frequency dividing or frequency filtering step, the average value slices (AIP) can be divided into low-pass filtered and high-pass filtered average value slices. The low-pass filtered average value slices can in particular comprise morphological structures.

In the high-pass filtering step, the maximum value slices can be filtered to form high-pass filtered maximum value slices. These can in particular comprise structures with high contrast or their edges and small objects, for example microcalcifications.

In the mixing step, high-pass filtered maximum value slices and high-pass filtered average value slices can be mixed to form mixed high-pass filtered maximum value slices. The mixing ratio can be freely selected or adapted. The mixing ratio can, for example, be 50/50- or 1:1. The mixed high-pass filtered maximum value slices can be displayed alternatively or additionally to the result slice images.

In the combining step, low-pass filtered average value slices can be combined with the mixed high-pass filtered maximum value slices to form the result slice images. Advantageously, the advantages of small slice thicknesses for morphological structures and the advantages of greater slice thicknesses for microcalcifications can be combined. Advantageously, individual microcalcifications per se and a possible grouping of microcalcifications can be identified in a simplified or more clearly depicted manner.

In the applying step, a moving maximum value can be applied across a predetermined/selected thickness of maximum value slices or across a predetermined/selected thickness of mixed high-pass filtered maximum value slices. The moving maximum value can in particular be a maximum value depicting a micro-calcium deposit from a maximum value slice, in particular extracted before application of the moving maximum value, which "runs along" across a plurality of successive result slices. In this way, the micro-calcium deposit and in particular a cluster of micro-calcium deposits can be more easily identified by the viewer. If the micro-calcium deposit were only depicted from the maximum value slice corresponding to the result slice, when viewing many slices in succession, the micro-calcium deposit would be briefly visible in one slice and would be easier to overlook. In addition, the spatial proximity to adjacent micro-calcium deposits in adjacent maximum value slices is easier to identify from the moving maximum value, since micro-calcium deposits from adjacent slices can be at least partially depicted together across one or more of result slices. The predetermined/selected thickness of maximum value slices or the predetermined/selected thickness of mixed high-pass filtered maximum value slices can in particular be a predetermined/selected multiple of the slice thickness of an average value slice. For example, the predetermined/selected thickness of the maximum value slices or the high-pass filtered maximum value slices may be greater by a predetermined/selected factor, in particular compared to the slice thickness of the average value slices. The predetermined/selected thickness or the predetermined/selected multiple or the predetermined/selected factor can be defined in the system or by the user, for example based on a breast thickness or a number of microcalcifications or other conspicuous structures within the region under examination or the breast.

The inventors have identified that the visibility of microcalcifications can be further improved. The concept of high-resolution slices can be applied to improve visibility with wide-angle recording. Here, a plurality of finer slice images can be generated for each output slice and then recombined with logic and combined to form an output slice. Due to the finer slices, it can be achieved that, in at least one of these slices, small microcalcifications are struck "sharply" and the contrast to the surroundings reaches its maximum as a result. The average value (AIP) and the maximum value (MIP) of the high-resolution slices relevant for the output slice are compared with one another and, if the difference is sufficient, the maximum value can be obtained instead of the average value.

The inventors have identified the following aspects. The perceptibility of microcalcifications can be improved by using a different (in particular increased) slice thickness, for very small objects (in particular higher frequencies), while the original slice thickness is retained for large objects (in particular medium to lower frequencies). This can be achieved by using a moving maximum value (moving MIP) across a defined thickness of maximum value slices (MIP slices) before these are combined with the average values in the next step.

A further aspect can be frequency-based combination of the high-resolution slices instead of the previous thresholding method. Here, high-frequency components of both the average value (AIP, short for average intensity projection) and the maximum value (MIP, short for maximum intensity projection) can be mixed together in a specific ratio and then combined with the low and medium-frequency components of the average value.

The solution to the problem can combine the advantages of wide-angle tomosynthesis (in particular better depth resolution) with those of small-angle tomosynthesis (in particular better perceptibility of microcalcifications). This enables lesions to be better differentiated from the surroundings than in pure small-angle tomosynthesis, but without having to forego the good identifiability in the case of microcalcifications.

If the so-called "moving MIP", i.e., the moving maximum value, is only applied to the MIP slices or the maximum value slices, the strength of the effect is reduced since the high-frequency components are then still combined with the high-frequency components of the AIP slices or the average value slices.

Alternatively, the "moving MIP", i.e., the moving maximum value, can also be applied to the combined high-frequency components, i.e., the mixed high-pass filtered maximum value slices in order to intensify the effect. Frequency-based combining can furthermore avoid a limit value for the difference, which increases the stability of the method.

According to at least one example embodiment, mask slices can be generated based on the tomosynthesis image data set. Artifact correction can be performed with respect to large high-contrast objects such as large calcium deposits or calcifications and/or metal. The mask slice can contain large high-contrast objects. According to at least one example embodiment, the mask slices can comprise macrocalcifications or metal objects. According to at least one example embodiment, the mask slices can comprise microcalcifications.

According to at least one example embodiment, the mask slices can be taken into account in conjunction with the maximum value slices. The maximum value slices can in particular show high frequencies, for example micro-calcium deposits and edges of high-contrast objects. Taking the mask images into account enables large high-contrast objects to be suppressed, for example large calcium deposits or metal objects. This can improve the visibility of micro-calcium deposits or microcalcifications.

According to at least one example embodiment, the slice thickness of a result slice image with a small object can be increased. According to at least one example embodiment, the (effective) slice thickness in a result slice image can be increased for a smaller object or a higher spatial frequency or frequency. This means that smaller objects or objects with higher spatial frequencies are transferred to adjacent result slice images. The result slice image can have a (standard) slice thickness. This obtains morphological information from precisely this (standard) slice thickness. With regard to the calcifications or small objects or high frequencies, the information is obtained from a slice thickness larger than the (standard) slice thickness, i.e., also from adjacent slices.

According to at least one example embodiment, the slice thickness of a result slice image with a larger object can correspond to a standard slice thickness. According to at least one example embodiment, the slice thickness in a result slice image for a larger object or a lower to medium spatial frequency can correspond to a standard slice thickness.

Alternatively, for larger objects, the slice thickness can be greater than the standard slice thickness. The, in particular effective, slice thickness for micro-calcium deposits or high frequencies can be greater than or equal to the slice thickness for large objects or medium frequencies, which in turn can be greater than the slice thickness for morphological structures or low frequencies.

The moving maximum value can also be applied to large objects or medium frequencies. The slice thickness for large objects and the slice thickness for microcalcifications can be different. The slice thickness for microcalcifications can in particular be greater than the slice thickness for large objects.

In the applying step, the maximum value, for example of a microcalcification, for example weighted by a Gaussian function, can be taken into account in the result slices. Maximum values further away from the result slice (depth) can be taken into account to a lesser extent than maximum values closer to the result slice (depth).

According to at least one example embodiment, the tomosynthesis data set can comprise projection data sets of a tomosynthesis recording. The tomosynthesis data set can in particular comprise a large number of projection data sets, recorded at a large number of projection angles.

According to at least one example embodiment, the step of generating average value slices (AIP) and maximum value slices (MIP) can comprise back projection of the projection data sets. Based on the projection data sets, a slice image data set can be generated by applying back projection. The average value slices and the maximum value slices can be generated based on the slice image data set.

According to at least one example embodiment, the maximum value, in particular for a microcalcification, can be displayed in a plurality of successive result slice images as a moving maximum value, while the information from the average value slices is in each case only displayed in the associated result slice. In this case, the maximum value can also be combined with an average value.

According to at least one example embodiment, the mixing ratio of the high-pass filtered maximum value slices and high-pass filtered average value slices can be 1:1. Alternatively, the mixing ratio can be freely selected or adapted.

According to at least one example embodiment, in a displaying step, the microcalcifications can be notified optically or acoustically.

Microcalcifications can be indicated or marked in the "main slice" in which they are located, for example, optically, graphically or the like. Herein, the main slice can in particular be the result slice in which the microcalcification is actually located. The result slice (depth) can, therefore, correspond to the depth of the microcalcification. The microcalcification can in particular be marked in the result slice corresponding to the maximum value slice in which the microcalcification is actually present as the maximum value.

The indication or marking can, for example, take place in the image, at the edge of the image, in the DICOM header, a secondary capture or the like, in particular with reference to the coordinates of the "smearing" of an activated moving maximum value of a high-contrast structure or its "moving along" in the adjacent slices. The coordinates can specify both x and y within the slice plane and the slice depth.

The method for determining the moving maximum value itself can be used as an indicator of the detection of a high-contrast structure (for example a micro-calcium deposit). This can take place as follows: with an activated moving maximum value, it can be established whether micro-calcium deposits are present (for example by comparing the slice images with a moving maximum value with those without a moving maximum value). Hence, it is possible to indicate in the slices or image that here such structures are displayed by the moving maximum value. It is now optionally possible to indicate informatively, in particular in advance, the (main) slices in which effects of a moving maximum value occur. The indicator function can be activated or deactivated so users can decide whether they wish to be notified of microcalcifications before viewing the results images or whether they first wish to view the result images impartially and, if necessary, receive the notifications on a repeat viewing. The marking can, for example, be in the form of a color. Alternatively or additionally, the marking can be shown by a graphical object, for example by outlining the microcalcification. When scrolling through the result slices, an acoustic notification of the presence of calcification in the (main) slice can be output to the user in the form of a short tone.

At least one example embodiment further relates to a mammography system for performing a method according to example embodiments. The advantages of the method according to example embodiments can advantageously be transferred to the mammography system.

A plurality of projection data sets can be recorded at a plurality of projection angles. Herein, the X-ray source can in particular be moved along a radius around a point in the breast, wherein a projection data set is recorded at each of the projection angles. During the recording, a patient's breast can be arranged as an examination object between an upper compression element and a lower compression element. The mammography system can further comprise a memory facility, a control facility and a computer unit. The mammography system can further comprise an input unit and an output unit, for example a screen.

At least one example embodiment further provides a computer program product with a computer program, which can be loaded directly into a memory facility of a control facility of an X-ray system, in particular in the form of the mammography system, with program sections for executing all the steps of a method according to example embodiments when the computer program is executed in the control facility of the mammography system.

At least one example embodiment further provides to a computer-readable medium on which program sections that can be read and executed by a computer unit are stored for executing all the steps of a method according to example embodiments when the program sections are executed by the mammography system.

FIG. 1 shows a method according to an example embodiment. The recorded projection data are back-projected in step 10. From this, maximum intensity projection/MIP slices (maximum intensity projection, MIP) can be generated in step MIP, average value intensity-projection/AIP slices (average intensity projection, AIP) can be generated in step AIP and mask slices can be generated in step 12. The mask slices can, for example, comprise macrocalcifications.

Based on the mask slices and the MIP slices, a moving maximum value (moving MIP) is applied in step 13. On the basis of this, a different (increased) slice thickness can be used for very small objects (higher frequencies, for example microcalcification), while the original or standard slice thickness can be retained for larger objects (medium to low frequencies). The moving MIP slices can be filtered with a high-pass filter in step 14 so that high-pass filtered MIP slices are generated. Alternatively, the moving maximum value can be applied to the mixed high-frequency components of the MIP and AIP.

A high-pass filter and a low-pass filter can be applied to the AIP slices in the steps 21 or 22 so that high-pass filtered and low-pass filtered AIP slices are generated. The low-pass filtered AIP slices contain the low-frequency and medium-frequency components of the average value.

The high-pass filtered AIP slices are mixed with the high-pass filtered MIP slices in step 15 to form mixed high-pass filtered MIP slices. Frequency-based mixing or combining of the high-resolution slices takes place instead of a thresholding method. The mixing takes place in a predetermined/selected ratio.

The mixed high-pass filtered MIP slices are combined with the low-pass filtered AIP slices in step 16 to form combined slices, the result slices. Advantageously, the identifiability of (micro)calcification can be improved.

The method according to at least one example embodiment generates result slice images with at least partially different slice thickness, in particular with respect to different (spatial) frequencies. The result slice images are generated based on a tomosynthesis image data set of a breast. The method has the following steps: in a generating step, average value slices AIP and maximum value slices MIP are generated based on the tomosynthesis image data set; in the frequency dividing step 21, 22, the average value slices AIP are divided or filtered into low-pass filtered and high-pass filtered average value slices; in the high-pass filtering step 14, the maximum value slices are filtered with a high-pass filter to form high-pass filtered maximum value slices; in the mixing step 15, high-pass filtered maximum value slices and high-pass filtered average value slices are mixed to form mixed high-pass filtered maximum value slices; in the combining step 16, the low-pass filtered average value slices are combined with the mixed high-pass filtered maximum value slices to form the result slice images; and in an applying step 13, 15, a moving maximum value is applied across a predetermined thickness of maximum value slices or across a predetermined thickness of mixed high-pass filtered maximum value slices.

Mask slices can be generated based on the tomosynthesis image data set. The mask slices can in particular comprise macrocalcification(s) or metal object(s). The mask slices can be taken into account in conjunction with the maximum value slices. This enables artifacts to be corrected or large objects to be disregarded.

The slice thickness is increased in a result slice image for a smaller object or a higher spatial frequency, while the slice thickness in a result slice image for a larger object or a lower to medium spatial frequency corresponds to a standard slice thickness or a slice thickness that is lower than the increased slice thickness. The maximum value, in particular for a microcalcification, is displayed in a plurality of successive result slice images as a moving maximum value, while the information from the average value slices is in each case only displayed in the associated result slice.

The tomosynthesis data set comprises projection data sets of a tomosynthesis recording. Before or in the step of generating average value slices AIP and maximum value slices MIP based on the projection data sets, back projection 10 of the projection data sets takes place.

The mixing ratio of the high-pass filtered maximum value slices and high-pass filtered average value slices can be 1:1 or alternatively be freely selected or predetermined.

In a displaying step, the microcalcifications can be notified optically or acoustically.

Figure 2:
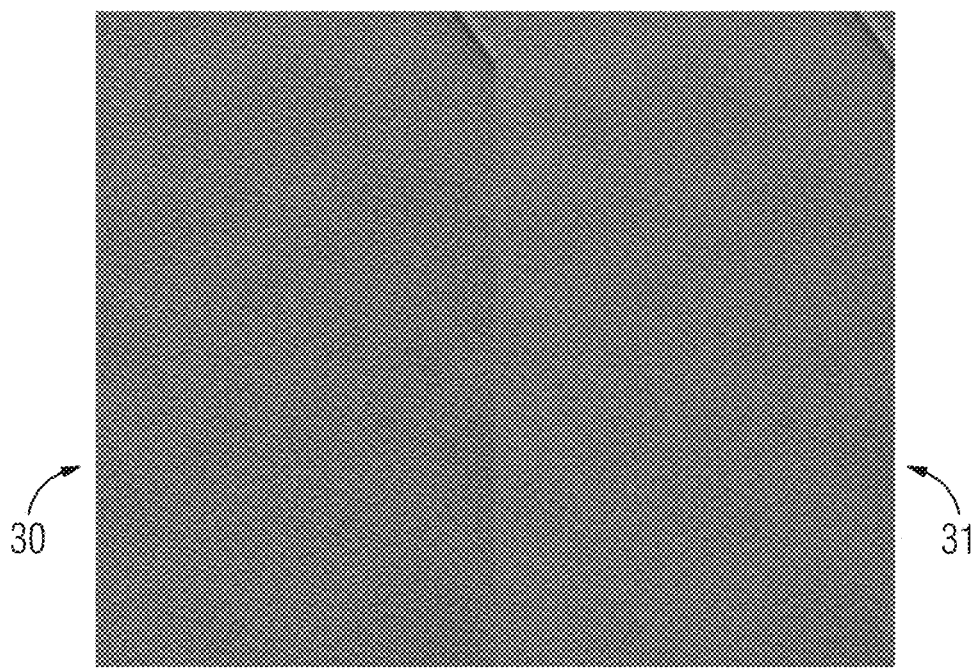
FIG. 2 shows at least one example embodiment for applying the method of FIG. 1 to the same data set with and without the application of the moving maximum value.

FIG. 2 shows an example embodiment of the method on the same data set with the application of the moving maximum value 31 and without the application of the moving maximum value 30. When the moving maximum value 31 is applied (w/moving MIP, righthand depiction), the microcalcifications remain visible for a longer time and the image noise is reduced. The visibility of the circular structures, similar to lesions, in the phantom remain identical.

Figure 3:
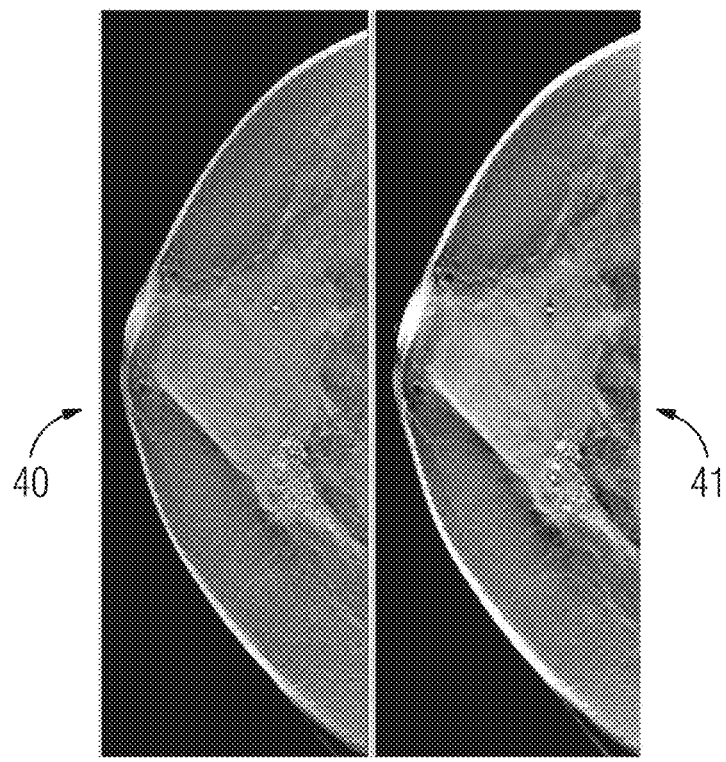
FIG. 3 shows a comparison of a known method with the method of FIG. 1 according to at least one example embodiment.

FIG. 3 shows a comparison of a known method with the method of FIG. 1 according to at least one example embodiment. The visibility of the microcalcifications can be significantly improved when using the method according to the at least one example embodiment 41 compared to a method without the features according to the at least one example embodiment 40.

FIG. 4 shows a mammography system according to at least one example embodiment. A plurality of projection data sets are recorded at a plurality of projection angles PI-1,0,1,2, . . . , 12. Herein, the X-ray source 2.1 is in particular moved along a radius around a point in the breast 8, wherein a projection data set is recorded at each of the projection angles PI-1,0,1,2, . . . , 12. During the recording, a patient's breast 8 is arranged as an examination object between an upper compression element 3.1 and a lower compression element 3.2.

Although example embodiments been illustrated in detail by at least some of example embodiments, example embodiments are not restricted by the disclosed examples and other variations can be derived herefrom by the person skilled in the art without departing from the scope of protection of example embodiments.

The invention claimed is:

1. A method for generating result slice images with at least partially different slice thickness based on a tomosynthesis image data set of a breast, the method comprising:
   generating average value slices and maximum value slices based on the tomosynthesis image data set;
   frequency dividing the average value slices into low-pass filtered and high-pass filtered average value slices;
   high-pass filtering of first maximum value slices to form high-pass filtered maximum value slices, the first maximum value slices being based on the maximum value slices;
   mixing the high-pass filtered maximum value slices and the high-pass filtered average value slices to form mixed high-pass filtered maximum value slices;
   combining the low-pass filtered average value slices with first mixed high-pass filtered maximum value slices to form the result slice images, the first mixed high-pass filtered maximum value slices being based on the mixed high-pass filtered maximum value slices; and
   applying a moving maximum value across a selected thickness of the maximum value slices to generate the first maximum value slices or across a selected thickness of the mixed high-pass filtered maximum value slices to produce the first mixed high-pass filtered maximum value slices.

2. The method as claimed in claim 1, further comprising: generating mask slices based on the tomosynthesis image data set.

3. The method as claimed in claim 2, wherein the mask slices comprise macrocalcifications or metal objects.

4. The method as claimed in claim 2, wherein the mask slices are used with the maximum value slices.

5. The method as claimed in claim 1, wherein the applying includes increasing a slice thickness in a result slice image an object or a relatively higher spatial frequency.

6. The method as claimed in claim 1, wherein the slice thickness in a result slice image for a relatively larger object or a relatively lower to medium spatial frequency corresponds to a standard slice thickness.

7. The method as claimed in claim 1, wherein the tomosynthesis data set comprises projection data sets of a tomosynthesis recording.

8. The method as claimed in claim 7, wherein the generating average value slices and maximum value slices comprises back projection of the projection data sets.

9. The method as claimed in claim 1, wherein the maximum value is displayed in a plurality of successive result slice images as a moving maximum value.

10. The method as claimed in claim 1, wherein a mixing ratio of the high-pass filtered maximum value slices and high-pass filtered average value slices is 1:1.

11. The method as claimed in claim 1, further comprising: displaying microcalcifications based on the result slice images.

12. A mammography system comprising a processor and a memory configured for performing the method as claimed in claim 1.

13. A non-transitory computer program product with a computer program, loaded directly into a memory facility of a control facility of a mammography system, with program sections when executed by the control facility cause the method of claim 1 to be performed.

14. A non-transitory computer-readable medium including program sections, when executed by a computer unit of a mammography system, cause the method of claim 1 to be performed by the mammography system.

15. The method as claimed in claim 3, wherein the mask slices are taken into account in conjunction with the maximum value slices.

16. The method as claimed in claim 2, wherein the applying includes increasing a slice thickness in a result slice image an object or a relatively higher spatial frequency.

17. The method as claimed in claim 5, wherein the slice thickness in a result slice image for a relatively larger object or a relatively lower to medium spatial frequency corresponds to a standard slice thickness.

18. The method as claimed in claim 1, wherein the maximum value is for at least one microcalcification.

19. The method as claimed in claim 2, wherein a mixing ratio of the high-pass filtered maximum value slices and high-pass filtered average value slices is 1:1.

20. A mammography system comprising a processor and a memory configured for performing the method as claimed in claim 2.

* * * * *